United States Patent [19]
Doersen et al.

[11] Patent Number: 5,286,645
[45] Date of Patent: Feb. 15, 1994

[54] RAT OSTEOSARCOMA CELL LINE OSR3TR1

[75] Inventors: Claus-Jens W. Doersen; Robert J. Isfort, both of Cincinnati, Ohio

[73] Assignee: The Procter & Gamble Company, Cincinnati, Ohio

[21] Appl. No.: 903,434

[22] Filed: Jun. 24, 1992

[51] Int. Cl.$^5$ .................... C12N 5/06; C12P 21/02
[52] U.S. Cl. .................. 435/240.2; 435/70.1; 435/240.1; 530/350
[58] Field of Search .............. 435/240.2, 240.1, 70.1; 530/350

[56] References Cited

U.S. PATENT DOCUMENTS

5,035,901  7/1991  Anderson et al. ............... 424/573

FOREIGN PATENT DOCUMENTS

0350641   1/1990   European Pat. Off. ...... A61K 37/02
2164042   3/1986   United Kingdom ........ A61K 37/00
WO91/18620 12/1991 World Int. Prop. O. ... A61K 37/02
WO91/18622 12/1991 World Int. Prop. O. ... A61K 37/36

OTHER PUBLICATIONS

Amitani, K., K. Ono, Y. Sakamato and Y. Nakata, "Osteogenic Induction by Cell-free Material from Murine Osteosarcoma and Its Cultured Cell Line", Gann, (Jun. 1975), vol. 66, No. 3, pp. 327–329.

Ikeda, S., S. Hiroshi, K. Akiyama, S. Watanabe, S. Ito, H. Inoue, H. Takechi, G. Tanabe and T. Oda, "Amplification of Both c-myc and c-raf-1 Oncogenes in a Human Osteosarcoma", Jpn. J. Cancer Res., (1989), vol. 80, pp. 6–9.

Miller, C. W., A. Aslo, C. Tsay, D. Slamon, K. Ishizaki, J. Toguchida, T. Yamamuo, B. Lampkin and H. P. Koeffler, "Frequency and Structure of p53 Rearrangements in Human Osteosarcoma", Cancer Research, (Dec. 1990), vol. 50, pp. 7950–7954.

Rodan, G. A. and M. Noda, "Gene Expression in Osteoblastic Cells", Critical Review Eukaryotic Gene Expression, (1991), vol. 1, Issue 2, pp. 85–91.

Rodan, G. A., J. K. Heath, K. Yoon, M. Noda and S. B. Rodan, "Diversity of the Osteoblastic Phenotype", Cell and Molecular Biology of Vertebrate Hard Tissues, (1988), Ciba Foundation Symposium 136, pp. 78–91.

Smith, H. S., "In Vitro Properties of Epithelial Cell Lines Established from Human Carcinomas and Nonmalignant Tissue", J. Natl. Cancer Inst., (Feb. 1979), vol. 62, No. 2, pp. 225–230.

Vukicevic, S., F. P. Luyten, H. K. Kleinman and A. H. Reddi, "Differentiation of Canalicular Cell Processes in Bone Cells by Basement Membrane Matrix Components: Regulation by Discrete Domains of Laminin", Cell, (Oct. 1990), vol. 63, pp. 437–445.

(List continued on next page.)

Primary Examiner—Robert J. Hill, Jr.
Assistant Examiner—Sally Teng
Attorney, Agent, or Firm—Brahm J. Corstanje; Milton B. Graff, IV; David L. Suter

[57] ABSTRACT

The present invention relates to a novel cell line isolated from a rat osteosarcoma having the following characteristics: A) a non-expressed p53 protein; B) a normal RB-1 gene as compared to a non-tumorigenic Sprague-Dawley rat cell control; C) a normal c-fos gene as compared to a non-tumorigenic Sprague-Dawley rat cell control; D) a 50-fold amplified c-myc gene as compared to a non-tumorigenic Sprague-Dawley rat cell control; E) a monolayer MATRIGEL ™ growth pattern; F) tumorigenic in nude mice; G) normal alkaline phosphatase activity; H) an ability to be serially propagated greater than fifty population doublings; I) an ability to produce a growth factor selected from the group consisting of: 1) a mesenchymal inhibitory growth factor; 2) a non-heparin binding mitogenic growth factor; 3) a first heparin binding mitogenic growth factor; 4) a second heparin binding mitogenic growth factor; 5) a third heparin binding mitogenic growth factor; and 6) a fourth heparin binding mitogenic growth factor.

The present invention also relates to growth factors produced by the novel cell line.

This invention also relates to a process for producing such growth factors.

1 Claim, 4 Drawing Sheets

OTHER PUBLICATIONS

Wrana, J. L., T. Kubota, Q. Zhang, C. M. Overall, J. E. Aubin, W. T. Butler and J. Sodek, "Regulation of Transformation-sensitive Secreted Phosphoprotein (SPPI/osteopontin) Expression by Transforming Growth Factor-$\beta$", Biochem. J., (1991), vol. 273, pp. 523–531.

1–"Bone-inducing agnet (BIA) from cultured human Saos-2 osteosarcoma cells", Anderson, H. C., K. Sugamoto, D. C. Morris, H. H. T. Hsu, & T. Hunt, Bone and Mineral, 16 (1992) pp. 49–62.

2–"Oncogene, Tumor Suppressor Gene, and Growth Signal Transduction Alterations in a Series of Chemically-Induced Rat Osteosarcomas", Isfort, R. J., D. C. Cody, G. Lovell, & C. J. Doersen, Poster Presentation, Seventh Annual Oncogene Meeting, Frederick, MD, Jun. 24, 1991.

3–"Growth Factors in Development, Transformation, and Tumorigenesis", Cross, M. and T. M. Dexter, Cell, vol. 64, pp. 271–280 (1991).

4–"Insulin Promotes Growth of the Cultured Rat Osteosarcoma Cell Line UMR–106–01:An Osteoblast–Like Cell", Hickman, J. and A. McElduff, Endocrinology, vol. 124, No. 2, pp. 701–706, (1989).

5–"Negative regulators of cell growth", Wang, J. L. and Y. M. Hsu, TIBS 11 (1986).

6–"Growth Factors: Mechanism of Action and Relation to Oncogenes", Heldin, C. H. and Westermark, B., Cell, vol. 37, pp. 9–20 (1984).

7–"Production of an Insulin-like Growth Factor by Osteosarcoma", Blatt, J., C. White, S. Dienes, H. Friedman and T. P. Foley, Jr., Biochemical and Biophysical Research Communications, vol. 123, No. 1, pp. 373–376, (1984).

Majeska et al., 1980, 107, 1494–1503, Endocrinology.

Wozney et al., 1988, 242, 1528–1534, Science.

Huang et al., 1988, 242, 1563–1566, Science.

Masuda et al., 1987, 84, 7716–7719, Proc. Natl. Acad. Sci.

Sturm et al., 1990, 50, 4146–4153, Cancer Research.

Chandar et al., 1992, 65, 208–214, British Journal of Cancer.

Isfort et al., 1992, 33, 111, Proceedings of the American Association for Cancer Res.

Figure 1a. OSR3TR1 Conditioned Media Heparin Agarose Chromatography

Figure 1b. OSR3TR1 Conditioned Medium Heparin Agarose Chromatography

Figure 2a. DEAE-Sephacel Chromatography of OSR3TR1 Heparin Agarose Flow Through.

Figure 2b. DEAE-Sephacel Chromatography of OSR3TR1 Heparin Agarose Flow Through.

RAT OSTEOSARCOMA CELL LINE OSR3TR1

TECHNICAL FIELD

This invention relates generally to a novel cell line, and specifically to a novel rat osteosarcoma cell line, as well as to certain growth factors produced by the cell line.

BACKGROUND OF THE INVENTION

Polypeptide growth factors play a key role in regulating the development of multicellular organisms and in the processes of tissue maintenance and repair. (see Cross and Dexter (1991) *Cell*, Vol. 64, pp. 271-280; Aaronson (1991) *Science*, Vol. 254, pp. 1146-1153.) At the cellular level, growth factors are involved in regulating proliferation and the progressive acquisition of the differentiated phenotype. Growth factors are capable of stimulating cellular proliferation as well as inhibiting cellular proliferation and many growth factors have been found to be multifunctional (Sporn and Roberts (1988) *Nature*, Vol. 332, pp. 217-219). The highly coordinated functions of growth factors is perhaps best exemplified in the development of the hematopoietic cell system (Metcalf (1989) *Nature*, Vol. 339, pp. 27-30) where a limited number of stem cells give rise to a larger population of developmental restricted progenitor cells. These progenitors cells are further stimulated to proliferate and differentiate into the mature lymphoid, erythroid and myeloid cells. A balance between cell types and numbers of cells must be maintained throughout the developmental cascade. This requires the concerted actions of growth factors which commit a cell (now developmentally restricted) along a particular cell lineage, of growth factors which stimulate the proliferation of committed cells, and finally, of growth factors which promote the differentiation of the committed cells and inhibit the proliferation of the mature, fully differentiated cells.

Tumor cells represent naturally occurring examples of cells where the processes that control cellular proliferation and differentiation have been uncoupled (Cross and Dexter (1991) *Cell*, Vol. 64, pp. 271-280; Aaronson (1991) *Science*, Vol. 254, pp. 1146-1153). The observation that many types of tumor cells secrete growth factors suggests that these factors can contribute to the tumorigenic process as well as normal cellular processes. Tumor cells have been found to secrete autocrine growth factors which stimulate the proliferation of the tumor cells themselves and paracrine growth factors which stimulate surrounding cells to secrete factors promoting the proliferation of the tumor cells. Paracrine factors can also stimulate the surrounding cells to provide a cellular environment promoting the survival of the tumor cells. For example, many types of tumor cells secrete growth factors that recruit endothelial cells and stimulate their proliferation and differentiation resulting in a new vasculature supplying nutrients for the tumor cells (Liotta et al., (1991) *Cell*, Vol. 64, pp. 327-336).

OBJECTS OF THE PRESENT INVENTION

It is an object of the present invention to provide a novel rat osteosarcoma cell line.

It is also an object of the present invention to provide novel growth factors having the characteristics of a mitogenic growth factor or an inhibitory growth factor.

It is also an object of the present invention to provide a process for producing novel growth factors from the cell line of the present invention.

SUMMARY OF THE INVENTION

The present invention relates to a novel cell line isolated from a rat osteosarcoma having the following characteristics: A) a non-expressed p53 protein; B) a normal RB-1 gene as compared to a non-tumorigenic Sprague-Dawley rat cell control; C) a normal c-fos gene as compared to a non-tumorigenic Sprague-Dawley rat cell control; D) a 50-fold amplified c-myc gene as compared to a non-tumorigenic Sprague-Dawley rat cell control; E) a monolayer MATRIGEL TM growth pattern; F) tumorigenic in nude mice; G) normal alkaline phosphatase activity; H) an ability to be serially propagated greater than fifty population doublings; I) an ability to produce one or more growth factors selected from the group consisting of: 1) a mesenchymal inhibitory growth factor; 2) a non-heparin binding mitogenic growth factor; 3) a first heparin binding mitogenic growth factor; 4) a second heparin binding mitogenic growth factor; 5) a third heparin binding Mitogenic growth; and 6) a fourth heparin binding mitogenic growth factor.

The present invention also relates to growth factors having the characteristics of growth factors isolated from the rat osteosarcoma cell line.

The present invention also relates to a process for producing a growth factor comprising: A) cultivating a cell line isolated from a rat osteosarcoma, and B) harvesting the growth factor.

The present invention also relates to a process for producing a growth factor comprising; a) isolating mRNA from an osteosarcoma cell line which codes from the growth factor, b) making cDNA of the mRNA, c) expressing the cDNA in an expression vector, and d) recovering the growth factor.

DETAILED DESCRIPTION OF THE INVENTION

As used herein "growth factor" means a protein which has an ability to stimulate proliferation of cells or to inhibit proliferation of cells.

As used herein "inhibitory growth factor" means a protein which has an ability to inhibit proliferation of cells.

As used herein "mitogenic growth factor" means a protein which has an ability to stimulate proliferation of cells.

As used herein, "tumorigenic" means an ability to form tumors in a host animal.

As used herein, "heparin agarose elution property of X M NaCl" means the molarity of NaCl used to achieve elution of a protein from heparin agarose column when a conditioned media comprising the protein is subjected to the heparin agarose column procedure described below, wherein X is a numerical value.

As used herein, "diethylaminoethyl elution property of X M NaCl" means the molarity of NaCl used to achieve elution of a protein from DEAE (diethylaminoethyl)-Sephacel column when flow through fraction from heparin agarose column comprising the protein is subjected to the DEAE-Sephacel column procedure described below, wherein X is numerical value.

As used herein, "OSR3TR1" refers to the novel cell line of the present invention, American Type Culture Collection (ATCC) No. CRL 11066.

As used herein, "OSR-2" means cell line ATCC CRL 11065.

As used herein, "w/v" and "v/v" mean percent by weight and percent by volume, respectively.

As used herein, "DEAE" means diethylaminoethyl.

The present invention relates to a novel cell line isolated from a rat osteosarcoma having the following characteristics: A) a non-expressed p53 protein; B) a normal RB-1 gene as compared to a non-tumorigenic Sprague-Dawley rat cell control; C) a normal c-fos gene as compared to a non-tumorigenic Sprague-Dawley rat cell control; D) a 50-fold amplified c-myc gene as compared to a non-tumorigenic Sprague-Dawley rat cell control; E) a monolayer MATRIGEL TM growth pattern; F) tumorigenic in athymic nude mice; G) normal alkaline phosphatase activity; H) an ability to be serially propagated greater than fifty population doublings; I) an ability to produce a growth factor selected from the group consisting of: 1) a mesenchymal inhibitory growth factor having the following characteristics: an ability to inhibit the proliferation of cells of mesenchymal origin, b) an inability to bind to heparin, and c) an inability to bind to diethylaminoethyl; 2) a non-heparin binding mitogenic growth factor having the following characteristics: a) an ability to stimulate proliferation of fibroblast cells, b) an ability to stimulate proliferation of osteoblastic cells, c) an inability to stimulate multipotent cells of mesenchymal origin, d) having a diethylaminoethyl elution property of from greater than 0 to about 0.2M NaCl, and e) an inability to bind to heparin; 3) a first heparin binding mitogenic growth factor having the following characteristics: a) an ability to stimulate proliferation of the fibroblast cells, and b) having a heparin agarose elution property of from greater than 0 to about 0.2M NaCl, 4) a second heparin binding mitogenic growth factor having the following characteristic: a) an ability to stimulate proliferation of fibroblast cells, b) an ability to stimulate proliferation of osteosblastic cells, c) having a heparin agarose elution property of from about 0.3 to about 0.7M NaCl; and 5) a third heparin binding mitogenic growth factor having the following characteristics: a) an ability to stimulate proliferation of fibroblast cells b) an ability to stimulate proliferation of osteoblast cells, and c) having a heparin agarose elution property of from about 1.0 to about 1.3M NaCl; 6) a fourth heparin binding mitogenic growth factor having the following characteristics: a) an ability to stimulate proliferation of fibroblast cells, b) an ability to stimulate proliferation of osteoblast cells, and c) having a heparin agarose elution property of from about 1.5 to about 1.7M NaCl.

Preferably, the cell line has the characteristics of American Type Culture Collection Accession No. CRL, 11066.

The present invention also relates to growth factors having the characteristics of the above-identified growth factors.

The present invention also relates to a method for producing one or more of the above-identified growth factors comprising: A) cultivating a cell line isolated from a rat osteosarcoma, and B) harvesting the growth factor. Preferably, the cell line has the characteristics of American Type Culture Collection Accession No. CRL 11066.

An alternative way of obtaining the growth factors produced by the cell line of the present invention is by isolation of the growth factor mRNA for use by those skilled in the art for expression of the protein of interest. Protein expression from mRNA covers a wide variety of techniques including PCR methodologies using a number of organisms for the final expression of the protein including bacteria, fungus, animal cells, insect cells and plant cells as well as noncellular protein expression methodologies (for an overall review of molecular biology techniques used in protein expression cloning see Sambrook et al. (1989) *Molecular Cloning—A Laboratory Manual,* 2nd edition, Cold Spring Harbor Laboratory Press, Cold Spring Harbor, N.Y.). Briefly, this method comprises isolating RNA from an osteosarcoma cell line which codes for the growth factor, making cDNA of the mRNA, expressing the cDNA in an expression vector, and recovering the growth factor. More preferably, this procedure involves isolation of mRNA from the osteosarcoma cell, making cDNA from the mRNA, cloning of the cDNA into an appropriate expression source, expression of the protein of interest from the cDNA inserted into the expression vector, screening the expression source for the protein of interest, purifying the expression clone containing the cDNA coding for the protein of interest, and expression of this purified cDNA in an expression vector in an appropriate expression source for large scale synthesis of the protein of interest. Multiple technical variations of this general expression schemes are well understood by those skilled in the art and all would apply.

The cell line of the present invention is useful as a biological source for the growth factors of the present invention and/or the mRNA coding for such growth factors. The growth factors of the present invention are useful for one or more of the following: 1) treating diseases affecting the bone and cartilage (e.g., those growth factors demonstrating an ability to stimulate osteoblast cells), 2) wound healing (e.g., those growth factors demonstrating an ability to stimulate fibroblast cells) and/or 3) cancer treatment (e.g., those growth factors demonstrating an ability to inhibit osteoblast, fibroblast and/or multipotent cells).

Statement of Deposit

OSR3TR1 has been deposited at The American Type Culture Collection, 12301 Parklawn Drive, Rockville, Md. 20852, U.S.A., on Jun. 5, 1992. The deposited strain has been assigned Accession No. CRL 11066.

The subject cultures have been deposited under conditions that assure access to the cultures will be available during the pendency of this patent application to one determined by the Commissioner of Patents and Trademarks to be entitled thereto under 37 CFR §1.14 and 35 USC §122. The deposits are available as required by foreign patent laws in countries wherein counterparts of the subject application, or its progeny, are filed. However, it should be understood that Applicant granting of permission to the depository to distribute samples of the deposit does not constitute an express or implied license to practice the invention claimed in any patent issuing on the subject application or any other patent.

The subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposits, and in any case, for a period of at least thirty (30) years after the date of deposit or for the enforceable life of any patent which may issue disclosing the cultures. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

Establishment of the OSR3TR1 Cell Line

A rat tumor cell line is established from a tumor excised from a Sprague-Dawley rat with osteosarcoma. The site of the excised tissue is the right tibia. The tumor tissue is aseptically remove from the euthanized animal and carefully trimmed of connective tissues. The tumor is minced in a culture dish (100 mm diameter) containing 15 ml of growth medium (10% fetal bovine serum, 90% RPMI 1640 medium (GIBCO)) further supplemented with penicillin (100 units/ml, GIBCO), Fungizone (0.25 micrograin/ml, GIBCO) and streptomycin (100 micrograms/ml,GIBCO), and incubated at 37° C. in an atmosphere of 5% $CO_2$ and 95% air with a relative humidity of approximately 95%. The adherent cells which migrated from the minced tumor pieces onto the surface of the culture dish are further expanded as a cell population using standard tissue culture techniques. Once the rat tumor cell line reaches confluence in a tissue culture flask (150 $cm^2$ surface area), the cell line is designated as having a mean population doubling of 1. At this stage, the cells are subcultured in growth medium (10% fetal bovine serum, 90% RPMI 1640 medium) with no antibiotic or antimycotic supplements. The rat tumor cell line is routinely tested for mycoplasma contamination by DAPI assay (Stanbridge (1981) Isr. J. Med. Sci., Vol. 17, pp. 563-568) and is found to be negative.

The rat tumor cell line is found to be poorly tumorigenic when assayed for tumor formation in congenitally athymic mice (a nude mouse, a product of Harlan Sprague Dawley, Inc.). The rat tumor cells at a mean population doubling of 8, are injected subcutaneously in the mid-flank region of the rat at an innoculum of approximately $1 \times 10^7$ cells per site. A total of eight sites (two per rat) are injected. Only one tumor arose at the site of injection. This tumor is aseptically excised from the euthanized rat and the tumor cell population is re-established in culture according to the methods described above for the establishment of the original tumor cell population. Once the cells reached confluency in a 150 $cm^2$ tissue culture flask, the cells are designated as OSR3TR1 at a mean population doubling of 1. These cells are found to be free of mycoplasma contamination by the DAPI assay (Stanbridge (1981) Isr. J. Med Sci., Vol. 17, pp. 563-568).

Characteristics of the OSR3TR1 Cell Line

The OSR3TR1 cell line can be serially propagated in culture with no known limited life span. The OSR3TR1 cell line displays a limited osteoblast-like phenotype in vitro. The cells show intense staining for the presence of alkaline phosphatase (Rodan and Rodan (1983) Bone and Mineral Research, Annual 2 (Peck, ed.) pp. 244-285) as detected by a cytochemical assay (Sigma Chemical Company, Procedure 85). It has been reported (Vukicevic et al., (1990) Cell, Vol. 63, pp. 437-445) that osteoblastic cells are capable of forming cell clusters exhibiting networks of canalicular cell processes when cultured on reconstituted basement membrane extracts such as MATRIGEL TM a solubilized tissue basement membrane available from (Collaborative Biomedical Products, Bedford, Mass., containing laminin, collagen type IV, heparin sulfate, proteoglycan and extactin). Fibroblasts, chondrocytes and embroyonic stem cells did not demonstrate the canalicular cell processes. OSR3TR1 cells when cultured on MATRIGEL TM at a density of approximately 50,000 cells per well of a standard 24-well tissue culture plate formed a monolayer of individual cells with no network of canalicular cell processes. This growth pattern is very different from the cell clusters with the characteristic canalicular processes that are formed by the osteoblastic MC3T3-E1 cells plated at an equivalent density (Sudo et al., (1983) J. Cell Biol., Vol. 96, pp. 191-198; Vukicevic et al., (1990) Cell, Vol. 63, pp. 437-445). The inability to form the canalicular network may be a property of the tumorigenicity of the OSR3TR1 cells.

The OSR3TR1 cell line is found to be highly tumorigenic when assayed for tumor formation in congenitally athymic mice (a nude mouse, a product of Harlan Sprague Dawley, Inc.). OSR3TR1 cells are injected subcutaneously in the mid-flank region of the animals at an innoculum of approximately $1 \times 10^7$ cells per site. A total of eight sites (two per animal) are injected, and tumors arose at 100% of the sites. Histologically, the tumors appeared to be fully differentiated osteosarcomas producing a boney mineralized extracellular matrix.

Molecular Characterization of the OSR3TR1 Cell Line

In order to characterize the OSR3TR1 cell line in terms of unique mutations which can identify this cell line we have screened the cell line for mutations in genes which are commonly mutated in osteosarcomas. This molecular fingerprint of the OSR3TR1 cell provides a convenient and useful way to identify this cell line because these mutations are critical for the growth of these cells and is not expected to change.

In this respect human osteosarcomas have been extensively studied with respect to mutations in the retinoblastoma (RB-1) and p53 tumor suppressor genes (Iavarone et al., (1992) Proc. Natl. Acad. Sci. USA, Vol. 89, pp. 4207-4209; Diller et al., (1990) Mol. Cell. Biol., Vol. 10, pp. 5772-5781; Masuda et al., (1987) Proc. Natl. Acad. Sci. USA, Vol. 84, pp. 7716-7719; Levine and Momand (1990) Biochem. et Byophys. Acta, Vol. 1032, pp. 119-136; Miller et al., (1990) Cancer Res., Vol. 50, pp. 7950-7954; Friend et al., (1987) Proc. Natl. Acad. Sci. USA, Vol. 84, pp. 9059-9063; Mulligan et al., (1990) Proc. Natl. Acad. Sci. USA, Vol. 87, pp. 5863-5867; Hansen et al., (1985) Proc. Natl. Acad. Sci. USA, Vol. 82, pp. 6216-6220; Horowitz et al., (1989) Science, Vol. 243, pp. 937-940; Toguchida et al., (1989) Nature, Vol. 338, pp. 156-158). RB-1 mutations include point mutations, deletions, and splicing mutations (Friend et al., (1987) Proc. Natl. Acad. Sci. USA Vol. 84, pp. 9059-9063; Levine and Momand, (1990) Biochem. et Biophys. Acta, Vol. 1032, pp. 119-136; Mori et al., (1990) Oncogene, Vol. 5, pp. 1713-1717; Horowitz et al., (1989) Science, Vol. 243, pp. 937-940). All of these mutations result in the production of a non-functional RB-1 protein. RB-1 is believed to function by acting as a "brake" on cellular proliferation at the appropriate time in the cell cycle. Control of the RB-1 function is achieved by selective and timely phosphorylation of RB-1 protein; phosphorylated RB-1 allows cellular proliferation while unphosphorylated RB-1 protein inhibits cellular proliferation (Laiho et al., (1990) *Cell*, Vol. 62, pp. 175-185; DeCaprio et al., (1989) *Cell*, Vol. 58, pp. 1085-1095; Buchkovich et al., (1989) *Cell*, Vol. 58, pp. 1097-1105; Chen et al., (1989) *Cell*, Vol. 58, pp. 1193-1198; Furukawa et al., (1990) *Proc. Natl. Acad. Sci. USA*, Vol. 87, pp. 2770-2774). RB-1 control of cellular proliferation is one part of a closely regulated network of cell cycle controls, which include the cell cycle control proteins c-myc, c-fos and TGF-B (Laiho et al., (1990) *Cell*, Vol. 62, pp. 175-185; Moses et al ., (1990) *Cell* Vol. 63, pp. 245-247; Robbins et al., (1990) *Nature*, Vol. 346, pp. 668-671).

The p53 tumor suppressor gene is originally identified as an SV40 large T antigen binding protein whose expression is greatly increased (approximately 5-100 fold at the protein level) during SV40 cellular transformation (Levine and Momand, (1990) *Biochem. et Biophys. Acta*, Vol. 1032, pp. 119-136; Levine et al., (1991) *Nature*, Vol. 351, pp. 453-456). The p53 gene has since been found to be mutated in a variety of tumor types (Hollstein et al., (1991) *Science*, Vol. 253, pp. 49-53) including human osteosarcoma cells (Mulligan et al., (1990) *Proc. Natl. Acad. Sci. USA*, Vol. 87, pp. 5863-5867; Miller et al., (1990) *Cancer Res.*, Vol. 50, pp. 7950-7954; Masuda et al., (1987) *Proc. Natl. Acad. Sci. USA*, Vol. 84, pp. 7716-7719; Diller et al., (1990) *Mol. Cell. Biol.*, Vol. 10, pp. 5772-5781). Mutation of the p53 gene either results in an altered protein which does not function normally or a complete loss of protein. Both of these mechanisms result in the absence of a functional p53 protein (Halevy et al., (1990) *Science*, Vol. 250, pp. 113-116; Chen et al., (1990) *Science*, Vol. 250, pp. 1576-1580; Milner and Medcalf, (1991) *Cell*, Vol. 65, pp. 765-774) and cellular transformation. The p53 protein is believed to function in several ways. The p53 protein is a transcriptional activator since p53 protein binds to specific DNA sequences (Raycroft et al., (1990) *Science*, Vol. 249, pp. 1049-1051; Kern et al., (1991) *Science*, Vol. 252, pp. 1708-1711) and contains an $NH_2$-terminal acidic domain which efficiently activates the transcription of genes in both yeast and mammalian cells (Fields and Jang, (1990) *Science*, Vol. 249, pp. 1046-1049). The protein produced from mutated p53 genes does not transcriptionally activate responsive genes (Raycroft et al., (1990) *Science*, Vol. 249, pp. 1049-1051). In addition, p53 regulates DNA replication since wild-type protein but not protein from mutated p53 genes associates with replication complexes (Levine et al., (1991) *Nature*, Vol. 351, pp. 453-456; Levine and Momand, (1990) *Biochem. et Biophys. Acta*, Vol. 1032, pp. 119-136) and is phosphorylated by p34(cdc2)-p60 and p34(cdc2)-cyclin B complexes (Bischoff et al., (1990) *Proc. Natl. Acad. Sci. USA*, Vol. 87, pp. 4766-4770; Milner et al., (1990) *EMBO J*, Vol. 9, pp. 2885-2889).

Two additional transforming genes which have been implicated in human and non-human osteosarcoma formation are the fos and myc oncogenes. The oncogenic variant of c-fos, v-fos, is first isolated as the transforming gene in retroviruses which resulted in murine osteosarcoma formation (Varmus (1984) *Ann. Rev. Genet.*, Vol. 18, pp. 553-612). Interestingly, transgenic mice carrying the v-fos oncogene display both cartilage and osteosarcoma tumors (Wang et al., (1991) *EMBO J*, Vol. 10, pp. 2437-2450). Oncogenic mutation of c-fos results when the fos gene is either over expressed or inappropriately expressed as a result of either viral transduction or mutation. C-fos functions in the cell, in conjunction with c-jun as the complex which binds the AP-1 transcriptional activation site (Abate et al., (1990) *Science*, Vol. 249, pp. 1157-1161; Sassone-Corsi et al., (1988) *Cold Spring Harbor Symposia on Quantative Biology LIII*, pp. 749-760).

C-myc has been found to be mutated both in radiation induced murine osteosarcomas (Sturm et al., (1990) *Cancer Res.*, Vol. 50, pp. 4146-4153) and in primary human osteosarcoma tumors (Bogenmann et al., (1987) *Cancer Res.*, Vol. 47, pp. 3808-3814). The myc oncogene is originally identified as the transforming gene in several retroviruses (v-myc) and c-myc mutations in a variety of tumor types are later identified (DePinho et al., (1987) *J. Cell Biochem.*, Vol. 33, pp. 257-266; Varmus (1984) *Ann. Rev. Genet.*, Vol. 18, pp. 553-612). C-myc is most commonly amplified or translocated, both of which, along with retroviral transduction, result in the inappropriate expression of the myc gene (Varmus (1984) *Ann. Rev. Genet.*, Vol. 18, pp. 553-612; DePinho et al., (1987) *J. Cell. Biochem.*, Vol. 33, pp. 257-266). Myc protein and the Max protein form a complex which binds the regulatory region of genes, via a unique sequence, to control their expression (Blackwood and Eisenman, (1991) *Science*, Vol. 251, pp. 1211-1217; Cole (1991) *Cell*, Vol. 65, pp. 715-716). C-myc, along with c-fos are immediate early genes and are believed to play a central role in mitogenic signalling in the cell (Rozengurt (1986) *Science*, Vol. 234, pp. 161-166).

An additional way to assay c-fos and c-myc functional activity is to determine if theses genes are transcriptionally activated following mitogenic stimulation. C-fos and c-myc are both members of a class of genes called the immediate early genes(Sassone-Corsi et al., (1988) *Cold Spring Harbor Symposia on Quantitative Biology LIII*, pp. 749-760; Depinho et al., (1987) *J. Cell. Biochem.*, Vol. 33, pp. 257-266). Genes in this class are transcriptionally activated following mitogenic stimuli usually within 1 hour and without the need of protein synthesis (Almendral et al., (1988) *Mol. Cell. Biol.*, Vol. 8, pp. 2140-2148; Greenberg et al., (1986) *Mol. Cell. Biol.*, Vol. 6, pp. 1050-1057). Since this is a complex pathway, alterations in immediate early gene transcription is indicative of either a mutation in the cellular pathway which leads from the receptor/plasma membrane to the gene/nucleus of the cell or a mutation which leads to the autocrine expression of a growth factor. Either of the above mutated phenotypes lead to a down regulation and subsequent inhibition of expression of the c-myc and c-fos genes following serum starvation and mitogen stimulation.

Characterization of Tumor Suppressor Genes and Oncogenes

High molecular weight DNA is isolated from the OSR-3TR cell line as follows. Approximately $1 \times 10^8$ cells are cultured as described above until confluent. These cells are then scraped off the tissue culture flask into culture media, collected by centrifugation at 3300 g for 5 minutes, the culture media is removed from the cell pellet and the pellet is resuspended in 9.5 ml of NET buffer (100 mM sodium chloride, 10 mM Tris—pH 8.0, 1 mM EDTA). To the resuspended DNA is added 50 ul of 10 mg/ml of proteinase K (Boehringer Mannheim) and 0.5 ml of 10% (w/v) sodium dodecyl sulphate/water. This mixture is mixed well and incubated at 55° C. for one hour followed by extraction twice with an equal volume of a 50:50 mixture of phenol:chloroform. The aqueous phase is collected by centrifugation at 3300 g for 5 minutes and reextracted with an equal volume of chloroform. The aqueous phase is collected by centrifugation at 3300 g for 5 minutes, removed to a new tube and to it is added 1 ml of 3M sodium acetate pH 5.2 and 20 ml of 100% ethanol. This solution is mixed well and incubated at −20° C. for 2 hours followed by the collection of high molecular weight DNA by centrifugation at 3300 g for 30 minutes. The high molecular weight DNA is washed once with 5 ml of 70 v/v.% (ethanol/water) dried and resuspended in TE (10 Mm Tris—pH 8.0 and 1 mM EDTA) at a concentration of 1 mg/ml.

For restriction enzyme analysis, 20 ug of the above isolated high molecular weight DNA in 20 ul TE is added to 2.5 ul of 10X restriction enzyme buffer (1X restriction enzyme buffer consist of 50 mM Tris—pH 8.0, 10 mM magnesium chloride, and 100 Mm sodium chloride) and 2 ul of restriction enzyme (either Eco R1 or Hind III at 10 units/ml both from New England Biolabs) and this mixture is incubated at 37° C. for 16 hours. Following incubation, the above solution is added to 3 ul of 10X gel loading buffer (10X gel loading buffer is 0.25% bromophenol blue, 0.25% xylene cyanol, 25% Ficoll type 400, 10 mM EDTA in water) and the restriction endonuclease generated fragments are separated by agarose gel electrophoresis. Agarose gel electrophoresis is performed as follows. A 0.6% (w/v) agarose (Bethesda Research Laboratories) gel in 1X TBE (1X TBE consist of 0.089M Tris, 0.089M boric acid, and 0.002M EDTA) is poured in a BioRad horizontal gel electrophoresis apparatus, the above DNA solution is loaded into a well and electrophoresis is performed in a IX TBE solution for 16 hours at 20 volts. Following electrophoresis, the gel is stained for 1 hour in 0.5 ug/ml ethidium bromide (Sigma Chemical Company)/water solution followed by photography under 302 nm ultraviolet light irradiation. The gel is then prepared for Southern blotting as follows. The gel is soaked for 1 hour in a solution of 1.5M sodium chloride and 0.5M sodium hydroxide with constant shaking followed by an incubation for 1 hour in a solution of 1.5M sodium chloride and 1M Tris—pH 8.0 with constant shaking. The gel is then transferred to an LKB Vacu-Blot apparatus (LKB Scientific) prefitted with a sheet of BAS-NC nitrocellulose (Schleiser and Schuel) and the transfer of DNA from the agarose gel to the nitrocellulose membrane is performed under 40 cm.H$_2$O of pressure using 10X SSC (10X SSC is 1.5M sodium chloride and 0.15M sodium citrate, pH 7.0) as the transfer medium. The OSR3TR1 DNA Southern blot is then used in a hybridization analysis as follows. The nitrocellulose filter is first wet in 6X SSC followed by prehybridization in hybridization buffer [50% formamide (molecular biology grade, Bethesda Research Laboratories), 5X Denhardt's solution (Denhardt's solution is 0.1% Ficoll, 0.1% polyvinylpyrrolidone, and 0.1% bovine serum albumin—pentax fraction V—all from Sigma Chemical Company), 5X SSPE (20X SSPE is 3M sodium chloride, 0.2M sodium phosphate, and 0.02M EDTA—pH 7.4), 0.1% sodium dodecyl sulphate, and 100 ug/ml of denatured salmon sperm DNA (Sigma Chemical Company)] for 4 hours at 42° C. with constant agitation. Molecular probes for the tumor suppressor genes RB-1 (ATCC #57450) and p53 (Levine and Momand (1990) *Biochemics et Biophysica Acta.*, Vol. 1032, pp. 119-136) and the oncogenes c-myc (ATCC #41008) and c-fos (ATCC #41040) are radiolabelled using an Amersham nick translation kit and [$^{32}$P]dCTP (ICN) to a specific activity of $1 \times 10(8)$ cpm/ug DNA by following the manufacturers recommendations. These radiolabelled probes are then added to the hybridization solution/nitrocellulose filter of the prehybridization step and incubated at 42° C. for 40 hours with constant agitation. Following hybridization, the nitrocellulose filters (blots) are first incubated in 2X SSC and 0.1% SDS at room temperature for 1 hour followed by an incubation in 0.2X SSC and 0.1% SDS at 65° C. for 1 hour. The results of the hybridization experiment are visualized by autoradiography at −70° C. Following autoradiography, the films are developed and used in data analysis.

The molecular analysis of the OSR3TR1 cell line RB-1, p53, c-myc and c-fos genes indicated that the RB-1, p53 and c-fos genes appeared normal (non-mutated, wild-type) as compared to a nontumorigenic Sprague-Dawley rat cell control at the above described level of analysis (restriction enzyme analysis and Southern blotting). The c-myc gene is amplified 50 fold as compared to a non-tumorigenic Sprague-Dawley rat cell control.

RB-1 and p53 Protein Analysis

Immunological identification of the p53 and RB-1 proteins are performed as follows. $1 \times 10^6$ OSR3TR1 cells are labelled for 4 hours with 100 uCi/ml of [$^{35}$S]methionine (TranSlabel - ICN) in methionine-free RPMI-1640 (GIBCO) media containing 10% fetal bovine serum for 4 hours at 37° C. Following labelling, the cells are scraped off the tissue culture plastic into the labelling media, the cells are collected by centrifugation at 3300 g for 5 minutes, followed by removal of the labelling media and the snap freezing of the cell pellet in liquid nitrogen. The frozen cell pellets are dissolved in 1 ml of ice-cold lysis buffer (50 mM Tris —pH 8.0, 5 mM EDTA, 150 mM sodium chloride, 0.5% Nonidet P-40, and 1 mM phenylmethylsulfonylfluoride) by vigorous vortexing and incubated on ice with intermediate vortexing for 30 minutes. The lysates are clarified of nonsoluable material by centrifugation at 10,000 g for 30 minutes, the supernate is removed to a new tube to which is added 10 ul of antibodies specific for either mutant p53 (Oncogene Science p53 Ab-3), normal and mutant p53 (Oncogene Science p53 Ab-1), or RB-1 (a 50:50 mixture of Oncogene Science RB Ab-2 and Ab-3), and 50 ul of a Protein A/G agarose (Boehringer Mannheim):lysis buffer (50:50). The above mixture is incubated overnight at 4° C. with constant shaking. The cell lysate is aspirated off and the antigen/antibody/protein A-G pellet is washed one time in 1 ml of lysis buffer, one time in 1 ml of SNTE buffer (50 mM Tris—pH 7.4, 5 mM EDTA, 5% sucrose—w/v, 1% Nonidet P-40, and 0.5M sodium chloride), and one time in 1 ml of RIPA buffer (50 mM Tris—pH 7.4, 150 mM sodium chloride, 1% Triton X-100, 0.1% sodium dodecyl sulphate and 1% sodium deoxycholate). Following washing, the antigen/antibody/protein A-G agarose pellet is redissolved in 25 ul of sample buffer (62.5 Mm Tris—pH 6.8, 2% sodium dodecyl sulphate, 10% glycerol, 5% 2-mercaptoethanol), boiled at 100° C. for 2-3 minutes, and applied to a well of a 10% SDS-PAGE gel. SDS- PAGE is performed as described by Laemmli (Laemmli, U.K. (1970) *Nature*, Vol. 227, pp. 680–685) for 6–8 hours at 30 mA constant current per gel. Following electrophoresis, the SDS-PAGE gels are incubated in 30% methanol and 10% acetic acid for at least 1 hours, impregnated with ENHANCE (NEN-DuPont) according to the manufacturers recommendations, dried onto Whatman 3 mm paper using a BioRad gel dryer set at 60° C. for 2 hours and autoradiography at −70° C. is performed.

The results of the p53 and RB-1 protein analysis of the OSR3TR1 cell line indicated that the p53 protein is deleted because we failed to detect p53 protein with either of the above described p53 antibodies. These results indicate that while the gene suffered no major alteration (deletion, duplication, etc) it had suffered a point mutation or a minor deletion which resulted in the loss of protein expression. The deletion of p53 protein in transformed cells has been observed previously (Levine et al., (1991) *Nature*, Vol. 351, pp. 453–456; Hollstein et al., (1991) *Science*, Vol. 253, pp. 49–53; Gannon et al., (1990) *EMBO J.*, Vol. 9, pp. 1595–1602; Diller et al., (1990) *Mol. Cell. Biol.*, Vol. 10, pp. 5772–5781). The RB-1 protein is normal both in its level of expression and its physical characteristics, indicative of a wild-type gene.

Immediate Early Gene Expression Following Mitogen Stimulation

In order to characterize the immediate early gene (c-myc and c-fos) transcription following mitogen stimulation in the OSR3TR1 cell line the following experiments are performed. Approximately $1 \times 10^8$ cells are grown to 70% confluence in a tissue culture flask in 25 ml of standard growth media. The cells are washed 2 times with serum-free media followed by the addition of 25 ml of serum-free culture media and incubated for 12–16 hours at 37° C. under an atmosphere of 10% carbon dioxide in an incubator. To the serum-starved cells is added 3 ml (10v/v.%) of fetal bovine serum and 10 ug/ml of cycloheximide and the cells are incubated as above for 3 hours. One group of cells is not mitogen stimulated and remained serum-starved. RNA from the mitogen stimulated and non-stimulated cells is isolated using the RNAzol (Cinna/Biotecx Inc.) methodology according to the manufacturer's recommendation. Briefly, $1 \times 10^8$ cells are lysed in situ with 10 ml of RNAzol, the lysate is collected, 1 ml of chloroform is added to the lysate, the samples are vortexed vigorously for 15 seconds, and the mixture is then centrifuged at 12,000 g (4° C.) for 15 minutes. The upper (aqueous) phase is transferred to a new tube, an equal volume of isopropanol is added to it, the samples are cooled to −20° C. for 45 minutes, followed by pelleting of the RNA by centrifugation at 12,000 g (4° C.) for 15 minutes. The pelleted RNA is washed once with icecold 70% ethanol/water, dried, and resuspended in RNAse-free water at 20 ug/4.5 ul. RNA formaldehyde agarose gel electrophoresis is performed as described (Sambrook et al., (1989) *Molecular Cloning*, Cold Spring Harbor Press, Cold Spring Harbor, N.Y.). Briefly, 20 ug of total cellular RNA is denatured by heating to 55° C. for 15 minutes in denaturation buffer [4.5 ul RNA solution, 2.0 ul 10X RNA gel buffer (0.2M MOPS—pH 7.0, 50 mM sodium acetate, and 10 mM EDTA), 3.5 ul formaldehyde and 10.0 ul formamide] followed by the addition of 2 ul of loading buffer (50% glycerol, 1 mM EDTA, 0.4% bromophenol blue, and 0.4% xylene cyanol) and loading of the sample into a well of the formaldehyde gel (1% agarose, 20 mM MOPS —pH 7.0, 5 mM sodium acetate, 1 mM EDTA and 2.2M formaldehyde). Electrophoresis is performed at 30 volts (constant voltage) for 16 hours. Following electrophoresis the gel is stained with ethidium bromide (0.5 ug/ml in water) for 1 hour, destained in water for 1 hour, and photographed under 300 nm ultraviolet light using a Foto/Prep I (Fotodyne) transilluminator. Following photography, the gel is transferred to nitrocellulose (Schleicher & Schuell, BA-S NC) using a LKB Vacugene vacublotting apparatus operating at 50 cm.H$_2$O with a 20X SSC (3M sodium chloride and 0.3M sodium citrate—pH 7.0) fluid transfer medium. Following transfer, the RNA is fixed to the nitrocellulose filter by UV irradiation using a Stratalinker (Stratagene Inc.) UV crosslinker at 0.12 Joules/cm$^2$. Following RNA fixation, the Northern blots are used in probe hybridization studies following previously described procedures (Sambrook et al., (1989) *Molecular Cloning*, Cold Spring Harbor Press, Cold Spring Harbor, N.Y.) that are modified as follows. The probes of interest, c-fos (ATCC #41040) or c-myc (ATCC #41008) are radioactively labelled by using an Amersham nick translation kit following the manufacturer's recommendations. Briefly, 1 ug of probe DNA is incubated with 1X nick translation buffer, 50 uCi alpha [$^{32}$p]-dCTP (NEN), and polymerase mix in a total volume of 20 ul at 15° C. for 2 hours followed by the addition of 80 ul of 1X STE (100 mM sodium chloride, 10 mM Tris—pH 8.0, and 1 mM EDTA). Separation of the incorporated from nonincorporated nucleotides is achieved using a Biospin column (BioRad). Typically 1 ug of probe had a specific activity of greater than $1 \times 10^8$ dpm. Following nick translation, the probe is boiled for 10 minutes and added to a prehybridized filter (4 hours in hybridization solution at 42° C.) in 10 ml of hybridization solution [6X SSPE (3M sodium chloride, 0.2M sodium phosphate—pH 7.4 and 20 mM EDTA), 5X Denhardt's solution (1% Ficoll, 1% polyvinyl-pyrrolidone, and 1% BSA—Pentax fraction V), 0.5% sodium dodecyl sulfate, 100 ug/ml denatured—sonicated salmon sperm DNA, and 50% formamide] and incubated for 48 hours at 42° C. Following hybridization the filters are washed at room temperature in 2X SSC—0.1% SDS followed by a wash at 65° C. with 0.2X SSC—0.1% SDS. The filters are then dried, mounted to 3MM paper (Whatman) and autoradiography at −80° C. is performed using intensifying screens (NEN).

The OSR3TR1 cell line displayed an altered immediate early gene response with a constitutive expression of c-myc, even in the absence of added growth factor, and an absence of transcriptional upregulation of the c-fos gene in response to mitogen stimulation.

Table 1 shows the characteristics of the OSR3TR1 cell line.

TABLE 1

Characterizations of the OSR-3TR1 Cell Line

The OSR-3TR1 cell line has the following characteristics;

A) a deleted p53 gene non-expressed p53 protein;
B) a normal RB-1 gene as compared to a non-tumorigenic Sprague-Dawley rat cell control;
C) a normal c-fos gene as compared to a non-tumorigenic Sprague-Dawley rat cell control;

D) 50-fold amplified c-myc gene as compared to a non-tumorigenic Sprague-Dawley rat cell control;
E) a monolayer MATRIGEL ™ growth pattern;
F) tumorigenic in nude mice;
G) alkaline phosphatase activity;
H) an ability to be serially propagated greater than fifty population doublings
I) an ability to produce the following growth factors:
 1) a mesenchymal inhibitory growth factor;
 2) a non-heparin binding mitogenic growth factor;
 3) a first heparin binding mitogenic growth factor;
 4) a second heparin binding mitogenic growth factor;
 5) a third heparin binding mitogenic growth factor; and
 6) a fourth heparin binding mitogenic growth factor.

Use of the OSR3TR1 Cell Line as a Source of Growth Factors

The ability of a growth factor to stimulate, or inhibit DNA synthesis in a serum-starved quiescent cell is perhaps the most widely studied response to growth factors. This ability to stimulate, or inhibit the mitogenic response of a target cell is an indicator of the growth factor's ability to stimulate, or inhibit cellular proliferation. The mitogenic response of cells can be quantitated using a [$^3$H]thymidine incorporation assay as previously described (Isfort (1990) *Somatic Cell Molec. Genet.*, Vol. 16, pp. 109–121). Briefly, target cells are plated at $2 \times 10^3$ cells/well in a 96 well microtiter plate and incubated overnight in growth medium to allow the cells to attach. The growth medium is removed and the cells are washed three times with phosphate buffered saline (GIBCO) followed by an 8 hour incubation in 50 ul/well of serum-free medium. Mitogens such as serum and various growth factors are added to the serum starved cells in a volume of 50 ul of medium, with serum-free medium serving as a control. After 16 hours incubation, the cells are exposed to 1 uCi [$^3$H] thymidine for 6 additional hours of incubation. The cells are then harvested and lysed on glass fiber filters using a PHD cell harvester (Cambridge Technology, Inc.) and the radioactivity in the samples is assayed by scintillation spectrophotometery.

To test for the secretion of mitogenic growth factors by OSR3TR1 cells, serum-free conditioned medium is harvested from cell cultures. OSR3TR1 cells are grown to confluency in a 150 cm$^2$ tissue culture flask. The growth medium is removed and the cell monolayer is rinsed three times with approximately 15 ml of phosphate buffered saline. The cells are then incubated in 25 ml of serum free medium for approximately 24 hours, and the conditioned medium is harvested and clarified by centrifugation for 15 minutes at 2000xg to remove cells and cellular debris.

To gain some information on the types of growth factors produced by OSR3TR1 cells, the clarified conditioned medium is fractionated by heparin agarose chromatography (type I heparin agarose, purchased from Sigma Chemical Company). The binding properties of a variety of growth factors to heparin has been reported (Shing et al., (1984) *Science*, Vol. 223, pp. 1296–1298; Klagsbrun and Shing (1985) *Proc. Natl. Acad. Sci. USA*, Vol. 82, pp. 805–809; Hauschka et al., (1986) *J. Biol. Chem.*, Vol. 261, pp. 12665–12674), thus allowing an empirical classification of the types of growth factors. After collecting the flow through fraction of the conditioned medium, heparin binding factors are eluted in a stepwise application of 0.2M NaCl, 1.0M NaCl, and 2.0M NaCl, all in 25 mM Tris buffer, pH8.0. All fractions are dialyzed versus water and lyophilized. For analysis of mitogenic activity, the lyophilized fractions are resuspended in 2.0 ml of serum free medium and sterilized by centrifugal filtration (Centrex filters, Schleicher and Schuell).

A panel of target cells is used which incorporated osteoblastic, fibroblastic and multipotential mesenchymal cell types. These include the osteoblastic cells OSR-2 (ATCC No. CRL 11065) and MC3T3-E1 (Sudo et al., (1983) *J. Cell Biol.*, Vol. 96, pp. 191–198); the fibroblastic cell line NIH-3T3 (American Type Culture Collection, CRL 1658); the fibroblastic cell line MRC-5 (American Type Culture Collection, CCL 171); the multipotential cell line C3H10T1/2, clone 8 (American Type Culture Collection, CCL 226); and the multipotential cell population isolated from neonatal rat muscle (designated NRM) according to slight modifications of the procedure describe by Sampath et al., (1984) *Proc. Natl. Acad. Sci. USA*, Vol. 81, pp. 3419–3423. Briefly, the tricep muscles are aseptically isolated from euthanized newborn Sprague-Dawley rats and cleaned of connective and vascular tissue. The muscles are minced and cultured in 15 ml of 10% fetal bovine serum, 90% CMRL-1066 medium (GIBCO) supplemented with antibiotics and antimycotic mixture (penicillin, 100 units/ml; streptomycin, 100 ug/ml; Fungizone, 0.25 ug/ml, GIBCO). Once the explant cultures reached confluence in a 150 cm$^2$ tissue culture flask, the NRM cell line is designated as being at mean population doubling of 1. The NRM cell line is capable of faming multinucleate myotubes in confluent cultures and can be stimulated by TGF-B1 to differentiate into chondrocyte-like cells (Seyedin et al., (1985) *Proc. Natl. Acad. Sci. USA*, Vol. 82, pp. 2267–2271).

The mitogenic responses elicited by the heparin agarose fractionated conditioned medium from OSR3TR1 cells are compared to a number of known growth factors. All growth factors are purchased from GIBCO BRL, Life Technologies, Inc., and are tested over a 3–4 log concentration range incorporating the effective concentrations suggested by the supplier. The growth factors are human recombinant platelet derived growth factor-AB heterodimer (PDGF-AB); human recombinant platelet derived growth factor-AA homodimer (PDGF-AA); human recombinant platelet derived growth factor-BB homodimer (PDGF-BB); human recombinant acidic fibroblast growth factor (aFGF); human recombinant basic fibroblast growth factor (bFGF); human recombinant epidermal growth factor (EGF); human recombinant insulin-like growth factor I (IGF-1); human recombinant insulin-like growth factor II (IGF-II); human recombinant transforming growth factor beta, type 1 (TGF-B1); human recombinant interleukin 1-beta (IL-1B); recombinant murine leukemia inhibitory factor (LIF); recombinant murine tumor necrosis factor alpha (TNF-a). In addition, a mixture of bone morphogenic proteins (BMP-2, BMP-3, BMP-4, and BMP-7) as isolated from bovine bone by Koenig et al., (1991) *J. Bone Mineral Res.*, Vol. 6, pp. 206 is included in the analysis. The BMPs have been shown to induce the formation of cartilage and bone in vivo (reviewed by Wozney (1989) *Progress in Growth Factor Research*, Vol . 1, pp. 267–280) and heparin affinity chromatography is used in the purification of the bone derived BMP mixture. The results of this analysis is shown in Table 2.

TABLE 2

Mitogenesis Results
Target Cell Line

| Stimulus | OSR2 (osteoblast) | MC3T3-E1 (osteoblast) | NRM (multipotent) | C3H10T1/2 (multipotent) | MRC-5 (fibroblast) | NIH3T3 (fibroblast) |
|---|---|---|---|---|---|---|
| 0% SERUM | 0 | 0 | 0 | 0 | 0 | 0 |
| 10% SERUM | + | + | + | + | + | + |
| PDGF-AA | + | + | + | + | + | ND |
| PDGF-BB | + | + | + | + | + | ND |
| PDGF-AB | + | + | + | + | + | + |
| EGF | + | + | + | + | + | + |
| aFGF | + | + | + | + | + | + |
| bFGF | 0 | + | + | + | 0 | 0 |
| IGF-I | + | + | + | + | + | + |
| IGF-II | + | + | + | + | + | + |
| TGF-B1 | + | (−) | 0 | + | 0 | + |
| IL-1B | + | + | + | + | ND | + |
| LIF | + | 0 | + | 0 | ND | 0 |
| TNF-a | + | + | + | ND | ND | + |
| BMP-2,3,4,7 | + | (−) | 0 | + | + | + |
| OSR3TR1 | | | | | | |
| HepAg FT | (−) | (−) | (−) | (−) | (−) | ND |
| 0.2 M NaCl | ND | 0 | + | 0 | + | ND |
| 1.0 M NaCl | + | 0 | + | 0 | + | ND |
| 2.0 M NaCl | + | + | + | + | + | ND |

Table Legend.
Comparison of proliferative effects of a variety of mitogens on target cells.
0 = no stimulation (equivalent to 0% serum control),
+ = mitogenic stimulation at least 50% above the 0% serum control,
− = inhibition of proliferation at least 50% of 0% serum control.
ND = not determined.

The results of the mitogenicity assay (Table 2) indicate that OSR3TR1 cells produce an inhibitory growth factor and three mitogenic growth factors that can be fractionated from the serum-free conditioned medium by heparin agarose chromatography. The inhibitory growth factor present in the heparin agarose flow through fraction appears to be a novel factor since none of the known inhibitory cytokines are reported to have such broad target cell specificity (Wang and Hsu (1986) *Trends Biochem. Sci.*, Vol. 11, pp. 24–26).

Mitogenic Growth Factors Produced by OSR3TR1 Cell line

For the larger scale generation of serum-free conditioned medium from OSR3TR1 cell cultures, the cell population is expanded to twenty 150 cm² flasks. After the cells reached confluency, the growth medium is decanted from the flasks, the attached cells are rinsed three times with approximately 15 ml of phosphate buffered saline, and 25 ml of serum-free medium per flask is added. The cell cultures are incubated at 37° C. for 24 hours in an atmosphere of 5%CO₂/95% air with a relative humidity of about 95%. The conditioned serum-free medium is harvested, clarified by centrifugation for 15 minutes at 2000 x g, and stored frozen at −20° C. The cell cultures are replenished with 25 ml of serum containing growth medium and cultured for one or two days. This recovery period is followed by another cycle of incubation in serum-free medium, as described above. Twelve cycles of serum-free medium incubation followed by serum containing growth medium recovery are employed and a total of about 6 liters of serum-free conditioned medium is collected.

Figure 1A:
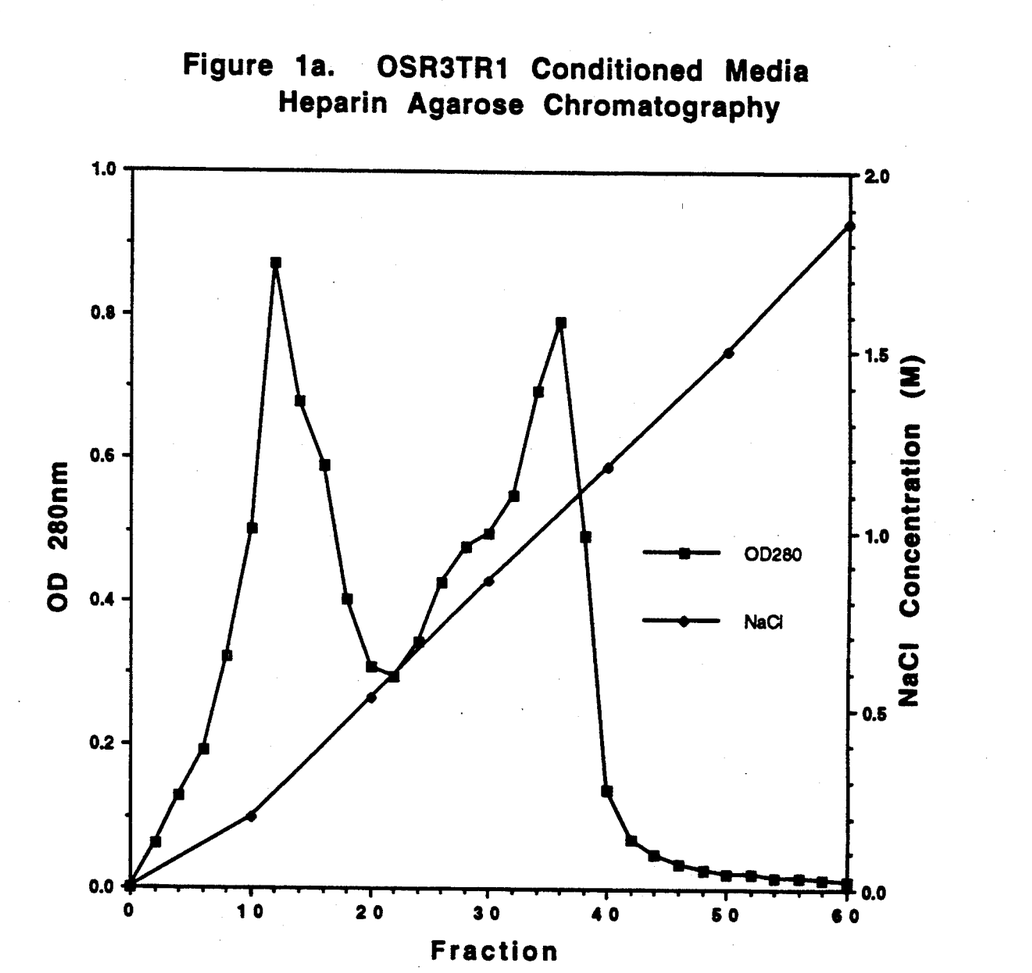
FIGS. 1a and 1b show results of the heparin agarose chromatography of OSR3TR1 conditioned medium.
Figure 1B:
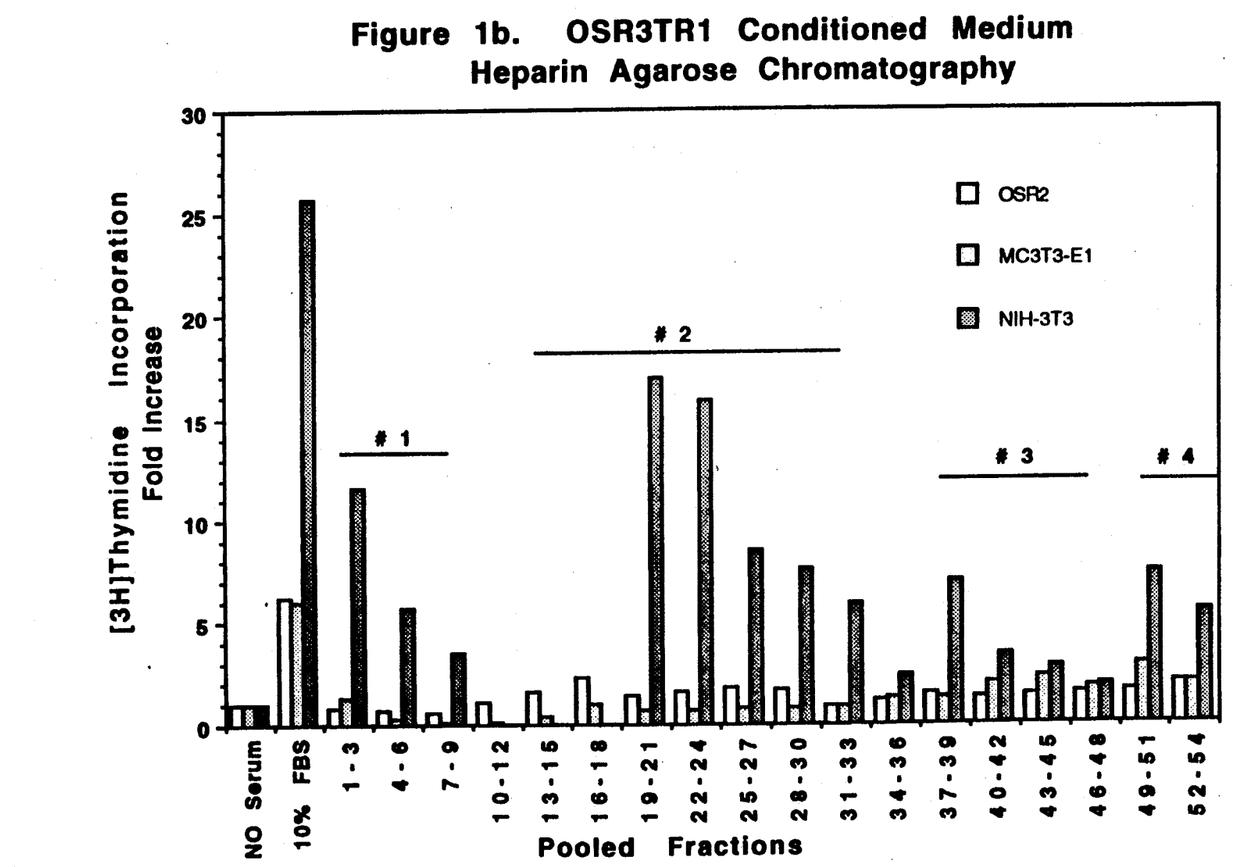

The frozen serum-free conditioned media harvested from OSR3TR1 cells is thawed and applied to a heparin agarose column (Type I, Sigma) with a bed volume of approximately 90 ml. After collecting the flow through fraction as successive one liter batches, proteins binding to the heparin agarose are eluted with a 1000 ml linear gradient of 25 mM Tris buffer, pH8.0, to 2.0M NaCl, 25 mM Tris buffer, pH8.0. Approximately 15 ml fractions are collected. Aliquots of 10 ml from the flow through and 1.0 ml from three consecutive fractions of the gradient are dialyzed against H₂O, and lyophilized. The lyophilized fractions are resuspended in 2.0 ml of serum-free medium, sterilized by centrifugal filtration (Centrex filters, Schleicher and Schuell), and assayed for mitogenic activity as described above. The osteoblastic OSR-2 cells (ATCC No. CRL 11065), the osteoblastic MC3T3-E1 cells (Sudo et al., (1983) *J. Cell Biol.*, Vol. 96, pp. 181–193) and the fibroblastic NIH-3T3 cells (American Type Culture Collection, CRL 1658) are used as target cells. The mitogenic response of cells is quantitated using a [³H]thymidine incorporation assay as previously described (Isfort (1990) *Somatic Cell Molec. Genet.*, Vol. 16, pp. 109–121). Briefly, target cells are plated at $2 \times 10^3$ cells/well in a 96 well microtiter plate and incubated overnight in growth medium to allow the cells to attach. The growth medium is removed and the cells are washed three times with phosphate buffered saline (GIBCO) followed by an 8 hour incubation in 50 ul/well of serum-free medium. The heparin agarose fractions are added to the serum starved cells in a volume of 50 ul of medium, with serum-free medium serving as a control and 20% FBS (10% FBS final concentration) serving as a positive mitogenic control. After 16 hours incubation, 10 ul of serum-free medium containing 1 uCi of [³H]thymidine (Amersham, 5 Ci/mmol, 185 MBq/mmol) are added to each well and the cells are incubated for 6 additional hours. The cells are then harvested and lysed on glass fiber filters using a PHD cell harvester (Cambridge Technology, Inc.) and the radioactivity in the samples is assayed by scintillation spectrophotometery. The data are calculated from the mean dpms of quadruplicate samples of the experimental groups and expressed as the fold incorporation relative to the serum-free treated cells. The heparin agarose fractionation of mitogenic growth factors from the serum-free conditioned medium of OSR3TR1 cells is shown in FIGS. 1a and 1b. The fractions containing the various heparin binding growth factors are indicated by a horizontal line. The fractions indicated by "#1", "#2", "#3", and "#4" indicate the first, second, third, and fourth heparin binding growth factors, respectively (FIG. 1b).

FIG. 1 shows the heparin agarose chromatography of OSR3TR1 conditioned medium. Panel a; absorbance at 280 nm of the pooled fractions is recorded, and NaCl concentration is determined by conductivity measurements of selected fractions. Panel b; mitogenic activity of the pooled fractions using OSR-2 cells, MC3T3-E1 cells, and NIH-3T3 cells (note, data for fractions 10-12, 13-15, 16-18, are not obtained for NIH-3T3).

Non-Heparin Binding Growth Factor Produced by OSR3TR1 Cell Line

Figure 2A:
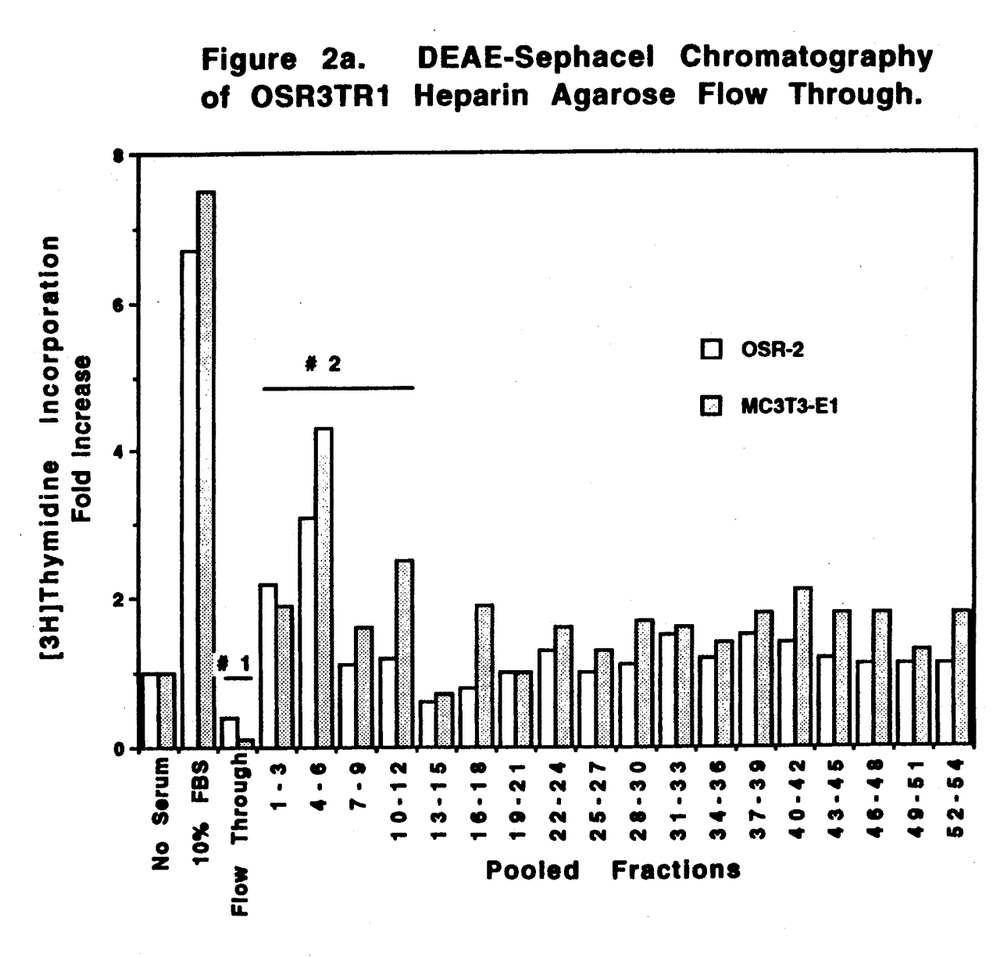
FIGS. 2a and 2b show results of the DEAE-Sephacel chromatography of the heparin agarose flow through fraction.
Figure 2B:
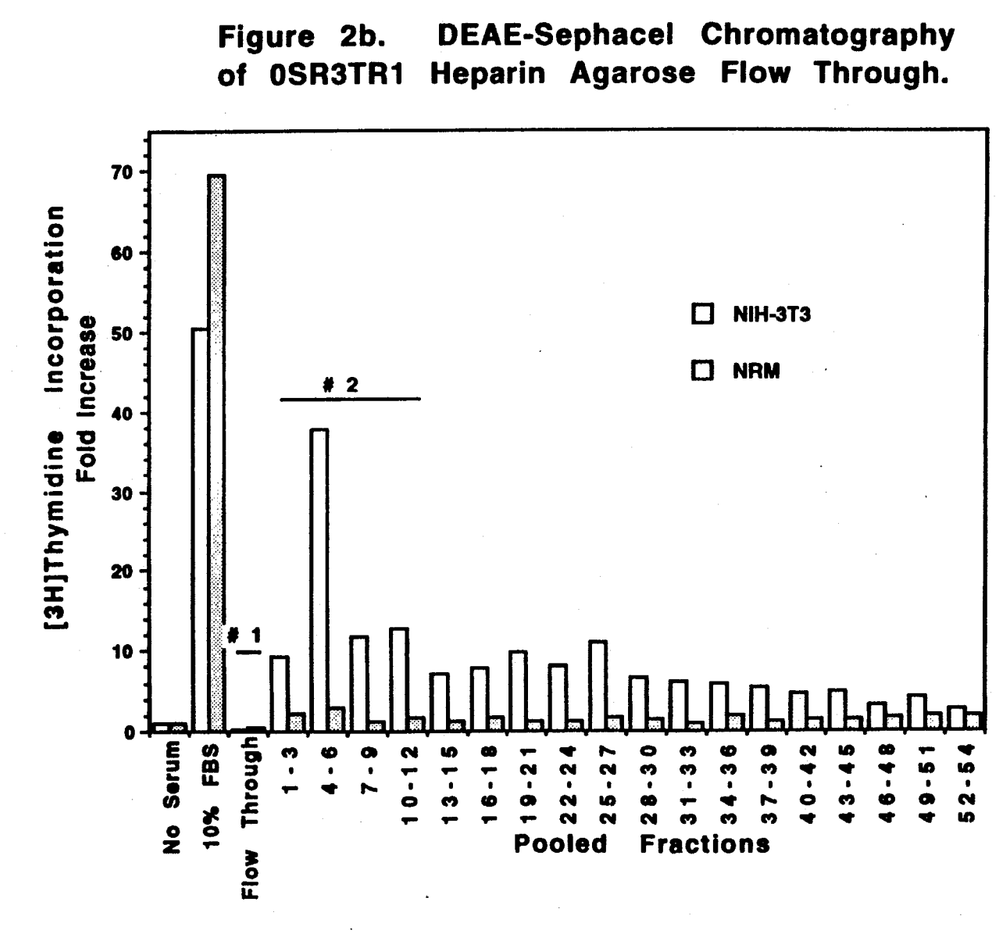

The heparin agarose flow through fraction in aforementioned process is concentrated from approximately 6 liters to 200 ml using an Amicon RU2000 spiral concentrator with a nominal molecular weight cut off of about 10 kDa. The concentrated flow through is diluted with 400 ml of 25 mM Tris buffer, pH8.0, and applied to a DEAE-Sephacel column (purchased from Sigma Chemical Company) with a bed volume of approximately 90 ml. After collecting the flow through fraction, the proteins bound to the DEAE-Sephacel column are eluted with a 1000 ml linear gradient from 25 mM Tris buffer, pH8.0, to 2.0M NaCl, 25 mM Tris buffer, pH8.0. Aliquots of 10 ml from the flow through and 1.0 ml from three consecutive fractions of the gradient are dialyzed against $H_2O$, and lyophilized. The lyophilized fractions are resuspended in 2.0 ml of serum-free medium, sterilized by centrifugal filtration (Centrex filters, Schleicher and Schuell), and assayed for mitogenic activity as described below. The osteoblastic OSR-2 cells (ATCC No. CRL 11065), the osteoblastic MC3T3-E1 cells (Sudo et al., (1983) *J. Cell Biol.*, Vol. 96, pp. 181–193), the multipotential NRM cell population (described above), and the fibroblastic NIH-3T3 cells (American Type Culture Collection, CRL 1658) are used as target cells. The mitogenic response of cells is quantitated using a [$^3$H]thymidine incorporation assay as previously described (Isfort (1990) *Somatic Cell Molec. Genet.*, Vol. 16, pp. 109–121). Briefly, target cells are plated at $2 \times 10^3$ cells/well in a 96 well microtiter plate and incubated overnight in growth medium to allow the cells to attach. The growth medium is removed and the cells are washed three times with phosphate buffered saline (GIBCO) followed by an 8 hour incubation in 50 ul/well of serum-free medium. The DEAE-Sephacel fractions are added to the serum starved cells in a volume of 50 ul of medium, with serum-free medium serving as a control and 20% FBS (10% FBS final concentration) serving as a positive mitogenic control. After 16 hours incubation, 10 ul of serum-free medium containing 1 uCi of [$^3$H]thymidine (Amersham, 5 Ci/mmol, 185 MBq/mmol) are added to each well and the cells are incubated for 6 additional hours. The cells are then harvested and lysed on glass fiber filters using a PHD cell harvester (Cambridge Technology, Inc.) and the radioactivity in the samples is assayed by scintillation spectrophotometery. The data are calculated from the mean dpms of quadruplicate samples of the experimental groups and expressed as the fold incorporation relative to the serum-free treated cells. The results of DEAE-Sephacel fractionation are shown in FIGS. 2a and 2b. FIG. 2a: mitogenic activity of the pooled fractions using OSR-2 and MC3T3-E1 as target cells. FIG. 2b: mitogenic activity of the pooled DEAE-Sephacel flow through fractions using NIH-3T3 and NRM as target cells. The fraction containing the mesenchymal growth inhibitory factor is indicated as #1. The fractions eluting from DEAE-Sephacel from more than 0 to about 0.2M NaCl containing the osteoblast/fibroblast growth factor are indicated as #2.

The results of these anaylses, together with the previous results from the small scale heparin agarose fraction of serum-free conditioned medium (Table 2) are summarized in Table 3.

TABLE 3

Summary of Growth Factors Secreted by OSR3TR1 Cells

1. A mesenchymal inhibitory growth factor which inhibits the proliferation in cells of mesenchymal origin. The mesenchymal inhibitory growth factor has an ability to inhibit the proliferation of cells of mesenchymal origin. The mesenchymal inhibitory growth factor does not bind to heparin agarose and does not bind to DEAE-Sephacel.
2. A non-heparin binding growth factor that preferentially stimulates the proliferation of osteoblastic cells and fibroblasts, but not multipotent cells of mesenchymal origin. The non-heparin binding growth factor binds to DEAE-Sephacel and elutes in the 0–0.2M NaCl range.
3. The first heparin binding growth factor present in the 0–0.2M NaCl eluate that preferentially stimulates the proliferation of fibroblasts.
4. The second heparin binding growth factor present in the 0.3–0.7M NaCl eluate that stimulates the proliferation of some osteoblastic cells (OSR-2 cells, ATCC No. 11065) and fibroblasts (NIH-3T3). This factor may be a member of the TGF-B/BMP family of growth factors.
5. The third heparin binding growth factor present in the 1.0–1.3M NaCl eluate that stimulates the proliferation of osteoblastic cells and fibroblasts. This factor may be a member of the FGF family of growth factors.
6. The fourth heparin binding growth factor present in the 1.5–1.7M NaCl eluate the stimulates the proliferation of osteoblastic cells and fibroblasts. This factor may be a member of the FGF family of growth factors.

The invention has been described herein with reference to certain preferred embodiments and examples. Obvious variations may appear to those skilled in the art. Therefore, the invention is not to be considered limited thereto but only by the claims which follow.

What is claimed is:

1. A cell line having all of the identifying characteristics of American Type Culture Collection Accession No. CRL 11066.

* * * * *

UNITED STATES PATENT AND TRADEMARK OFFICE
CERTIFICATE OF CORRECTION

PATENT NO. : 5,286,645

DATED : February 15, 1994

INVENTOR(S) : C. J. W. Doersen and R. J. Isfort

It is certified that error appears in the above-identified patent and that said Letters Patent is hereby corrected as shown below:

Column 5, line 25, "micrograin" should read --microgram--.

Column 6, line 10, "extactin" should read --entactin--.

Column 6, lines 10 and 11, "embroyonic" should read --embryonic--.

Column 10, line 3, "Biochemics" should read --Biochemica--.

Column 14, line 31, "faming" should read --forming--.

Column 15, line 14 of Table 2, "0 + + + 0 0" should read --0 + 0 + 0 0--.

Signed and Sealed this

Eighteenth Day of April, 1995

Attest:

BRUCE LEHMAN

Attesting Officer

Commissioner of Patents and Trademarks